United States Patent

Wallisch

[11] 4,262,201
[45] Apr. 14, 1981

[54] APPARATUS FOR DETERMINING THE SPECIFIC WEIGHT OF SELECTED REGIONS OF MICROSCOPIC SMALL PLANE PARALLEL SAMPLES

[75] Inventor: Karl Wallisch, Vienna, Austria

[73] Assignee: Oesterreichische Studiengeseilschaft für Atomenergie G.m.b.H., Vienna, Austria

[21] Appl. No.: 967,858

[22] Filed: Dec. 8, 1978

[30] Foreign Application Priority Data

Dec. 21, 1977 [AT] Austria .................................. 9179/77

[51] Int. Cl.³ ........................ G01N 23/00; G21F 5/04
[52] U.S. Cl. .................................... 250/360; 250/511
[58] Field of Search .................. 250/308, 358 R, 359, 250/360, 511, 512, 513

[56] References Cited

U.S. PATENT DOCUMENTS

| | | | |
|---|---|---|---|
| 2,932,391 | 4/1960 | Broekhuysen | 250/308 |
| 3,767,931 | 10/1973 | Williams | 250/511 |
| 3,955,086 | 5/1976 | Tsujii et al. | 250/359 |

Primary Examiner—Alfred E. Smith
Assistant Examiner—Janice A. Howell
Attorney, Agent, or Firm—Werner W. Kleeman

[57] ABSTRACT

An apparatus for determining the specific weight of selected regions of microscopic small, for instance of a size between about 5 μm to 1 mm, approximately plane parallel samples by means of a substantially punctual radiation source for γ or X-rays, containing a first collimator, an observation device provided with incident light illumination, a sample stage having a sample carrier and a standard for the specific weight being movable perpendicular to the axis of the beam of the punctual radiation source, and a radiation measuring device for determination the absorption of radiation. There is provided a second collimator having a smaller opening than the first collimator, and as radiation measuring device there is provided a measuring probe and a countrate measuring device for a predetermined wavelength.

14 Claims, 5 Drawing Figures

APPARATUS FOR DETERMINING THE SPECIFIC WEIGHT OF SELECTED REGIONS OF MICROSCOPIC SMALL PLANE PARALLEL SAMPLES

BACKGROUND OF THE INVENTION

The present invention relates to a new and improved construction of apparatus for the determination of the specific weight of selected regions of microscopic small, for instance of a size between about 5 μm to 1 mm, approximately plane parallel samples.

The determination of the specific weight of selected regions of samples particles is of utmost significance for many technological fields of application, since such quite often constitutes a significant characteristic for the presence of certain properties.

In the case of gas-cooled high-temperature reactors there are employed for the retention of fission products at the fuel kernels having a size between 100 and 800 μm essentially pyrocarbon layers as the enveloping or sheathing material. Pyrocarbon material can be produced so as to have different properties and different specific weights by varying the deposition parameters and the gas employed for coating at the thermal decomposition. The pyrocarbon layers which are employed with fuel particles must be capable of withstanding the different effects during the irradiation. This is possible by selecting suitable layers. Directly around the core there is applied an approximately 30 to 100 μm thick porous carbon layer. The function of this carbon layer is to provide free volumes or spaces for the reception of the core swells as well as for the gaseous fission products caused by burn-off. Following this so-called "buffer layer" is one or a number of layers, specifically heavier layers formed of dense pyrocarbon, possibly also silicon carbide, having a thickness of 70 to 150 μm, the function of which is, on the one hand, to prevent diffusion of the fission products out of the kernel, and, on the other hand, to form a pressure vessel for the gaseous fission products. In the last few years there have been developed a number of measuring methods and techniques for quality control of pyrocarbons, extensively rendering possible testing of the material properties.

One of the major material parameters is the specific weight. There are available for this determination a number of measuring methods, which essentially are either predicated upon the determination of the volume and related mass, or employed the technique of immersion of the layer to be measured in a liquid of known or determinable density. These values of the specific weight are always the average or mean specific weight of the layers over a number of layer fragments or also entire layers.

According to a further process there is mechanically rubbed off at a large number of particles the layer in stages of 10 to 20 μm and by differential measurements there is determined the specific weight from the mass and volume change. The thus obtained profile constitute mean values derived from many similar layers. Owing to the relatively large measuring inaccurance this technique is less suitable. It does however provide additional information regarding the layer homogenity.

The value of the momentary outermost layer of the particle can be determined relatively simply and positively. Yet even here there must be taken into account that the conventionally employed immersion technique produces too high density values owing to the penetration of the immersion liquid into the open pores.

Up to the present time, due to the absence of any possibility of carrying out a density measurement with high local resolution, it is still completely unclear to what extent the density fluctuation in deposition direction influences the radiation behavior of the layer. However, from the irradiation behavior of pyrocarbon layers of different starting density, it is possible to conclude that by virtue of density fluctuations mechanical stresses are formed in the layer. Depending upon the pyrolysis gas there are made, in accordance with a dose of about $2 \times 10^{21}$ EDN, final densities which attain the same values either completely independent of the starting density, at least extensively approach such, or assume even contrary values. In any event, with such changes of the specific weight there arise appreciable volume changes which endanger the stability of the coating.

From the scientific fields of biology and metallurgy there are known X-ray absorption microscopes, by means of which it is possible to determine the specific weight of selected regions of microscopic small, approximately plane parallel samples. Such microscopes, as a rule, comprise an X-ray unit and a light microscope by means of which there are illuminated by incident light illumination the sample to be examined. The region to be determined is moved into the image field of the light microscope, since as a rule the optical axis of the X-ray unit coincides with that of the light microscope. In conjunction with a standard there is taken an X-ray picture of the sample. The standard is step-like in its construction, so that different blackening of the film occurs, depending upon the step height. Since the blackening, among other things, is dependent upon the mass of the sample, it is possible with known layer thickness of the sample to draw certain conclusions regarding the specific weight, and the different blackenings allow by means of the standard an extrapolation of the specific weight of the sample.

The determination of the specific weight by means of an X-ray shadow or shadow projection microscope, wherein it is possible to determine the specific weight due to blackening of a film, apart from the complicated nature of determining the specific weight in this manner, further is associated with the drawback that between the exposure intensity and blackening there exists an additional logarithmic correlation which can be affected by the development. Hence, even with small irregularities there can arise large errors.

SUMMARY OF THE INVENTION

Hence, with the foregoing in mind it is a primary object of the present invention to provide a new and improved construction of apparatus enabling as simply and accurately as possible the determination of the specific weight of microscopic small, essentially plane parallel sample particles.

The inventive apparatus for the determination of the specific weight of selected regions of microscopic small, for instance 5 μm to 1 mm, approximately plane parallel sample particles, comprises a substantially punctual radiation source for γ or X-ray radiation, at least a first collimator, an observation device with incident light illumination, a sample stage with sample carrier and standard for the specific weight being movable perpendicular to the axis of the beam cone of the punctual radiation source and a radiation measuring device for measuring the absorption. According to the invention, there is provided a second collimator having a smaller opening than the first collimator and as the radiation measuring device there is provided a measuring probe as well as a count rate-measuring device for a predetermined wavelength.

With such type equipment it is possible to determine the specific weight in an exceedingly rapid and simple fashion. By means of the opening of the further or second collimator there is defined the region where there should be determined the specific weight and due to the use of a measuring probe with a count rate-measuring device for a certain wavelength there can be carried out computation of the specific weight by means of the count rates.

According to the invention the second collimator has a number of openings which are movable at the path of the rays of the punctual radiation source. Preferably there are provided at the observation device a marking corresponding to the related collimator opening. In this way there can be carried out particularly simple measurements of different, for instance different large regions, and at the same time there is possible an optical observation at the corresponding region.

If the collimators are arranged between the sample and the measuring probe, then there also can be observed during the analysis particularly small regions.

Another notable advantage resides in the fact that if the openings of the second collimator are rectangular, then there is possible an accommodation to the different sample shapes and to the different arrangement of the sample structures. Thus, for instance, in the case of spherical-layer shaped precipitants it is possible to select the rectangular collimator openings such that it only detects a layer, thereby rendering possible exact measurement results over a larger region of the sample.

If the sample is movable through the beam of the punctual source as a function of the specific weight of the sample region located in the beam, then also in the case of large differences in specific weight there can be obtained great accuracy, since, for instance, the region of a sample can be retained within the path of the light rays or beam for such time until there has been obtained a certain total count of pulses.

If a standard for the specific weight serves as the sample carrier, then there can be carried out at any time and in rapid fashion a comparison measurement, without having to remove the sample from the equipment.

If the standard has the same thickness as the sample at the region of the sample, then it is not necessary to determine the thickness of the sample, rather it is possible to directly derive from the counting rate the specific weight. In this way there can be accomplished a particularly rapid and exact determination of the specific weight. A particularly slight difference during the counting rates of standard and sample allows for an extremely great accuracy during the determination, which thus can be attained in that the standard is formed of the same chemical material as the region of the sample which is to be analysed.

A preferred embodiment of the inventive apparatus resides in the fact that the measuring probe comprises a scintillation counter which preferably is connected with a process control, thus allowing an accommodation to the momentarily required sensitivity merely by changing the amplification and without any complicated equipment expenditure.

BRIEF DESCRIPTION OF THE DRAWINGS

The invention will be better understood and objects other than those set forth above, will become apparent when consideration is given to the following detailed description thereof. Such description makes reference to the annexed drawings wherein.

DETAILED DESCRIPTION OF THE PREFERRED EMBODIMENTS

Figure 1:
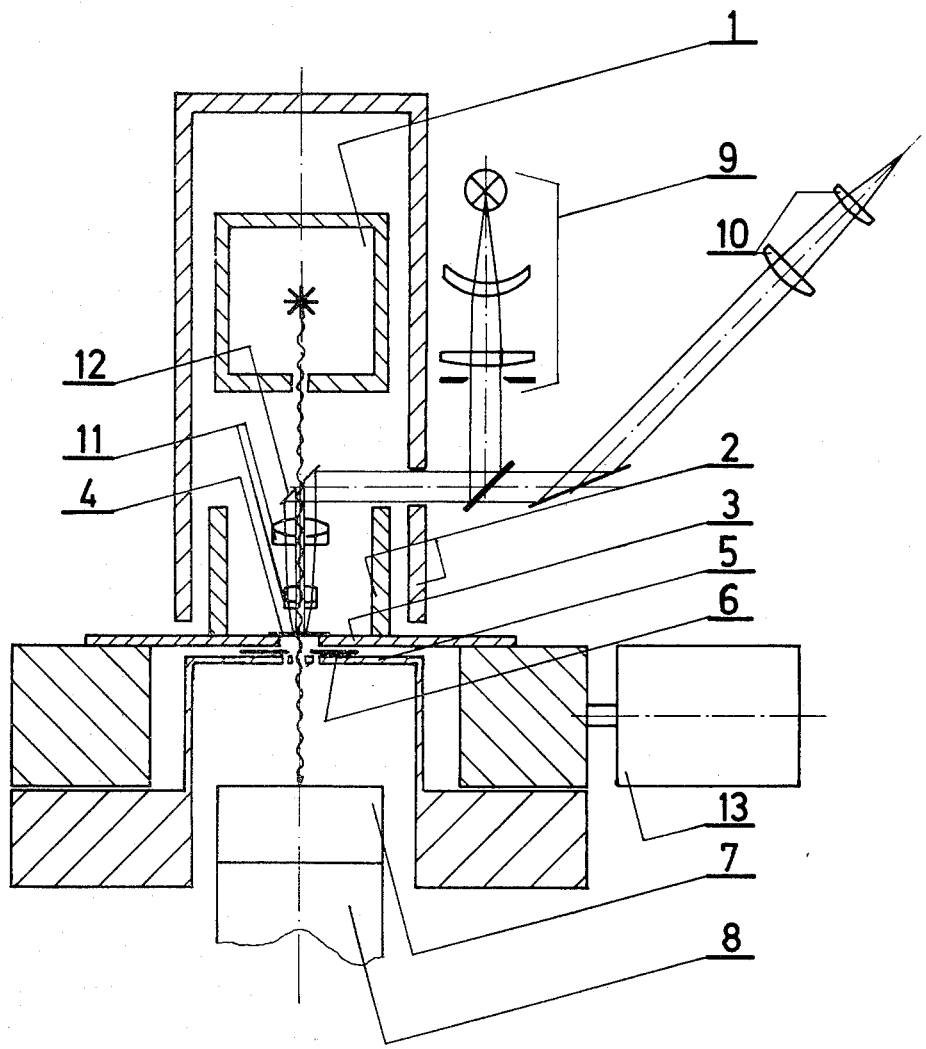
FIG. 1 is a schematic illustration of an density measuring device having a scintillation counter.

Describing now the invention in detail, the intensity I of X-ray radiation, after passing through a sample, is calculated by means of the following equation:

$$I = I_0 \cdot e^{(-\mu \cdot d)} \qquad (1)$$

wherein:

$I_0$ = intensity of the incident radiation;

$-\mu$ = absorption coefficient; and d = sample thickness.

In the energy region of 4.9 keV (characteristic titanium radiation) or 5.9 keV (chromium radiation), interesting for the measurement of carbon, the absorption due to photoelectric effects is dominant, so that the absorption coefficient $\mu$ extensively corresponds to the photo-absorption coefficient $\tau$, wherein $\tau$ is dependent upon the density $\rho$, the employed wavelength $\lambda$ and the atomic number Z of the material. This can be expressed by the following equation:

$$\tau = k_1 \cdot \rho \cdot \lambda^3 \cdot Z^3 \qquad (2)$$

Since during the measurement $\lambda$, Z and d are maintained constant, it is possible to derive from the above equation (1) the following:

$$I = I_0 \cdot e^{(-k_2 \cdot \rho)} \qquad (3)$$

With microsectioning there is employed a standard of known density ($\rho_{ref}$), so that after determination of $I_0$ and I there can be computed the constant $k_2$. This can be expressed by the following equation:

$$-k_2 = \frac{\ln \cdot \left(\frac{I}{I_0}\right)}{\rho \text{ ref.}} \qquad (4)$$

The specific weight of a layer thus can be calculated, by measurement of the relevant residual intensity, according to the following:

$$\rho = \frac{\ln \cdot \left(\frac{I}{I_0}\right)}{-k_2} \qquad (5)$$

Figure 3:
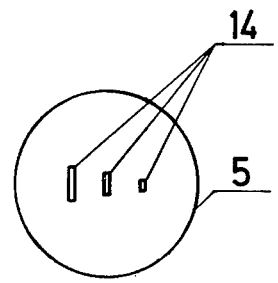
FIG. 3 illustrates a collimator.

The density measuring apparatus illustrated in FIG. 1 will be seen to comprise a substantially punctual X-ray radiation source 1 which is surrounded by a radiation shield 2. The radiation shield 2 essentially extends up to the region of a sample table 3 at which there is arranged a sample carrier or support 4 containing a sample. Below the not particularly referenced sample there are located the collimators 5 and 6. The collimator 5, which is located close to the measuring probe 7, has smaller openings 14 (see FIG. 3) than the collimator 6 and as shown in FIG. 3 can possess a number of different measuring openings 14 which are arrangable at the path of the rays or beams. By displacing the collimator 6 there can be freed in each case different measuring openings. Below the collimators 5 and 6 there is arranged the measuring probe 7 having a photomultiplier 8. The measuring probe 7 is a sodium iodide scintillator. The sample at the sample carrier 4 is illuminated by a direct illumination device 9. Observation of the sample is accomplished by means of a suitable observation device having an occular 10, which has a marking corresponding to a collimator opening 14 and, for the instance, formed by a diaphragm, as well as objective 11. The reflector or mirror 12 serving for observation and illumination and the objective 11 are bored-through, so that the X-rays can reach the sample without being attenuated. The sample table 3 can be moved by a stepping motor 13.

Figure 2:
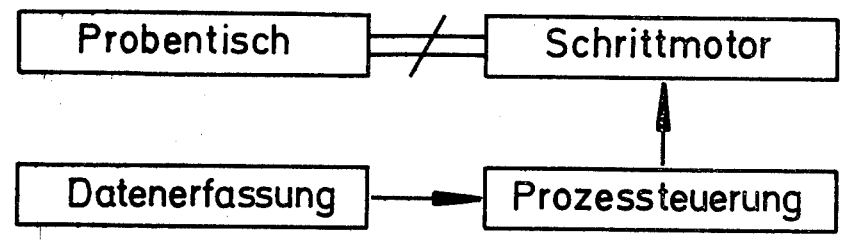
FIG. 2 is a block circuit diagram of the process control.

The block circuit diagram, illustrated in FIG. 2, for controlling the sample table operates in the following manner: the data registrator comprises a detector having a measuring probe and a photomultiplier, a preamplifier and main amplifier for amplification of the electronic pulses, a single-channel analyser which selects the pulses of a predetermined energy which are then summated in a counter. There is determined the time which is necessary to record, for instance, 100,000 pulses. This time span constitutes a coefficient of measure for the specific weight which can be computed from the thus resulting residual intensity according to the prior given equation (5), if by means of measurement of the standard there are determined the values $k_2$ and also $I_0$. Now if there have been recorded for instance 100,000 pulses, then by means of the process control the stepping motor is controlled such that the next sample region can be analysed, so that there can be obtained a profile of the specific weight and, if desired, such information stored. A reproduction of the stored values can be obtained, for instance, by means of a recorder, display or the like. For certain fields of application, for instance medical purposes (thin tissue sections), it can be of interest to only indicate the differences of the specific weight, and the different regions with the same specific weight are reproduced in each case with one color, for instance, in a multiple color writer or recorder.

The collimator shown in FIG. 3 is in the form of a cap which is arranged over the sodium iodide crystals and has different rectangular measuring openings 14 which, by shifting the collimator 6 (FIG. 1), in each case can be covered such that only one measuring opening is located in the path of the rays or radiation.

Figure 4:
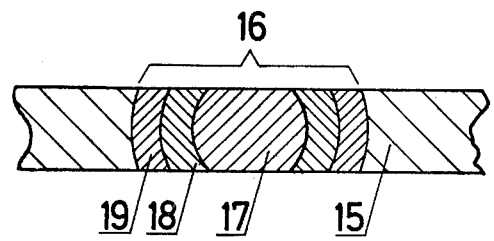
FIG. 4 illustrates a sample with a sample carrier.

Now in FIG. 4 there is shown in sectional view a sample carrier 15 with samples 16. The sample carrier or support 15 and the sample 16 are produced in the following manner:

A number of bores having a diameter of about 1 millimeter are formed at a carbon plate having a diameter of about 12 millimeters and a thickness of about 1.5 millimeters. Pressed into these bores are the samples which are to be processed and having approximately spherical shape. Thereafter, both the sample and also the sample carrier or support are cut into a thin section i.e., microsection at a precision end face cutting or grinding machine having a diamond pot disk or the like.

The samples 16 have a core 17 containing nuclear fuel which is surrounded by two layers 18 and 19 of pyrocarbon.

Figure 5:
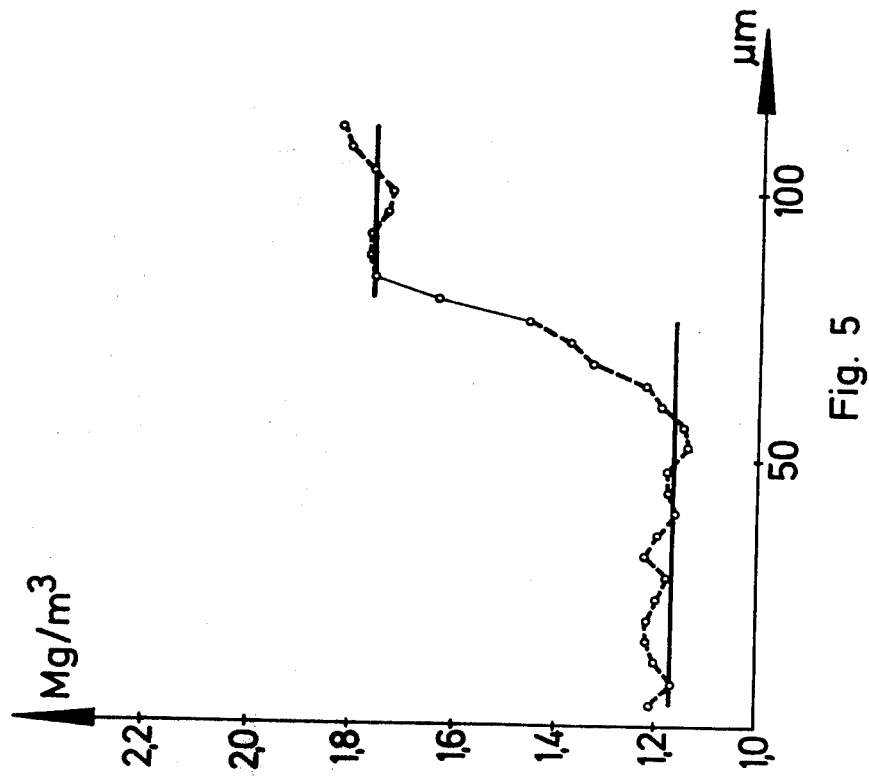
FIG. 5 illustrates a graph of measurements of the specific weight.

The graph shown in FIG. 5 was obtained by a sample of the type shown in FIG. 4. The sample is moved by means of the stepping motor such that initially the layers 18 and then the layer 19 are analysed. The densities at the individual layers are different as a function of the distance from the center. The inner layer with a density of 1.17 g/cm$^3$ has a relatively porous structure, whereas the second layer having a mean or average specific weight of 1.76 g/cm$^3$ already is a dense layer. As will be apparent from the graph, there is present a slow continuous transition from the porous to the dense layer.

The following values show that the determination of the specific weight by means of the inventive apparatus is more accurate and associated with less systematic errors than the density measurement by means of microradiography or according to the suspension method.

Determination by microradiography: for irradiating a thin section of a sample of dense carbon there is employed unfiltered chromium radiation with an excitation potential of 20 kV. The photographic recordation is accomplished by means of Kodak "high resolution plates". The microradiographies are evaluated at a microscope "Reichert MeF", equipped with a transmitted light illumination and microphotometer.

Determination of the density according to the suspension method: In a beaker glass there was placed bromoform in which there was immersed the sample. Then there was added isobutanol until the sample floated. From the quantities of bromoform and isobutanol and their specific weights there was calculated the specific weight of the mixture and thus the sample.

EXAMPLE 1

By means of the suspension method there was determined the specific weight of a dense carbon, and the mean or average value, derived from five values or measurements, gave a weight of 1.575 g/cm$^3$ with a standard deviation of 0.005. The value according to microradiography, likewise derived from five measuring values, resulted in a specific weight of 1.583 g/cm$^3$ and a standard deviation of 0.011.

With the inventive apparatus employing an X-ray radiation source with 4.9 keV and a measuring collimator of $5\times100\mu$ there was likewise derived from five measuring values a specific weight of 1.572 g/cm$^3$ with a standard deviation of 0.005.

EXAMPLE 2

For porous carbon there was determined on the basis of its weight and its geometric dimensions a specific weight of 1.16 g/cm$^3$ with a standard deviation of 0.005.

The value for the specific weight according to the suspension method was determined from five values and amounted to 1.70 g/cm$^3$ and with a standard deviation of 0.02. This large deviation is explainable by virtue of the fact that the liquid partially penetrated into the sample body and thus simulated a higher specific weight.

With the inventive apparatus, based upon five measuring values, there was determined a specific weight of 1.163 g/cm$^3$ with a standard deviation of 0.005.

As will be apparent from the above explanations, the inventive apparatus also was suitable for the determination of specific weights even when other techniques partially fail, and there can be obtained a relatively great accuracy. There can be used for analysis purposes radiation having a wavelength of 0.1 Å to 7 Å.

While there are shown and described present preferred embodiments of the invention, it is to be distinctly understood that the invention is not limited thereto, but may be otherwise variously embodied and practiced within the scope of the following claims. ACCORDINGLY,

What I claim is:

1. In an apparatus for determining the specific weight of selected regions of microscopic small, approximately plane parallel samples, of a size between about 5 μm to 1 mm, comprising a punctual radiation source for γ or X-ray radiation, a first collimator having at least one opening, an observation device having incident light illumination, a sample stage with a sample carrier and standard for the specific weight, said sample stage being movable perpendicular to the axis of the beam cone of the punctual radiation source, a radiation measuring device for determining the radiation absorption, the improvement which comprises:

a second collimator having a smaller opening than the first collimator; and said radiation measuring device comprising a measuring probe and a count rate-measuring device for a predetermined wavelength.

2. The apparatus as defined in claim 1, wherein: both of said collimators are arranged between the sample and the measuring probe.

3. The apparatus as defined in claim 1, wherein: said second collimator has a number of openings movable in the path of the beam of the punctual radiation source.

4. The apparatus as defined in claim 3, further including:

marking means corresponding to the relevant collimator opening arranged at the observation device.

5. The apparatus as defined in claim 4, wherein: said marking means comprise aperture means corresponding to the relevant collimator opening.

6. The apparatus as defined in claim 3, wherein: the openings of the second collimator are substantially rectangular.

7. The apparatus as defined in claim 1, further including:

means for moving the sample through the beam of the punctual source as a function of the specific weight of the sample region located in the path of the beam.

8. The apparatus as defined in claim 1, wherein: the standard for the specific weight serves as the sample carrier.

9. The apparatus as defined in claim 8, wherein: the standard has essentially the same thickness as the sample at the region of the sample.

10. The apparatus as defined in claim 8, wherein: said standard is formed of the same chemical material as the region of the sample to be analysed.

11. The apparatus as defined in claim 1, wherein: said measuring probe comprises scintillator crystal means.

12. The apparatus as defined in claim 1, further including:

process control means connected with said measuring probe.

13. The apparatus as defined in claim 7, further including:

process control means connected with said measuring probe; and said process control means serving to control the movement of the sample through the path of the beam of radiation.

14. In an apparatus for determining the specific weight of selected regions of microscopically small, approximately plane parallel samples, of a size between about 5 μm to 1 mm, comprising a punctual radiation source for γ- or X-ray radiation, a first collimator having at least one opening, an observation device having incident light illumination, a sample stage with a sample carrier and standard for the specific weight, said sample stage being movable perpendicular to the axis of the beam cone of the punctual radiation source, a radiation measuring device for determining the radiation absorption, the improvement which comprises:

a second collimator having a smaller opening than the first collimator both of said collimators being arranged between the sample and the measuring probe, whereby said second collimator has a number of openings movable in the path of the beam of the punctual radiation source; and said radiation measuring device comprising a measuring probe and a count rate-measuring device for a predetermined wavelength.

* * * * *